United States Patent [19]

Gray et al.

[11] 3,996,224

[45] Dec. 7, 1976

[54] MANUFACTURE OF CYANURIC ACID

[75] Inventors: Charles A. Gray, Princeton; Sidney Berkowitz, Highland Park; James Lawrence Manganaro, E. Windsor, all of N.J.

[73] Assignee: FMC Corporation, Philadelphia, Pa.

[22] Filed: Dec. 9, 1975

[21] Appl. No.: 638,988

[52] U.S. Cl. .......................................... 260/248 A
[51] Int. Cl.$^2$ ..................................... C07D 251/32
[58] Field of Search ............................... 260/248 A

[56] References Cited

UNITED STATES PATENTS 3,835,136   9/1974   Hirdler et al. ..................... 260/248

*Primary Examiner*—John M. Ford

[57] ABSTRACT

Waste digester liquor, containing dissolved triazines and iron, is treated with ammonia until the pH is about 2.5 to 4 thereby precipitating most of the triazines while leaving most of the iron in solution. The triazines are separated and recycled back to the digester. The filtrate of ammonium salts is useful as a source of fertilizer nitrogen.

6 Claims, No Drawings

MANUFACTURE OF CYANURIC ACID

This invention relates to the manufacture of cyanuric acid. More particularly, it is concerned with recovering useful and valuable products from the aqueous waste streams associated with such manufacture.

Cyanuric acid is an important chemical commodity, the principal use of which is in the production of chlorinated cyanurates, a family of commercial dry bleaches. In fact, current industry sources estimate that 90% of the total output is converted to chlorinated derivatives while the remainder finds application as a chlorine stabilizer for swimming pools and as a starting material for organic syntheses.

Although obtainable by a variety of reactions, cyanuric acid is made commercially from the pyrolysis of urea in accordance with the following scheme:

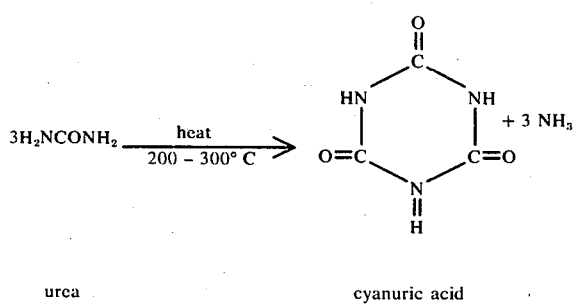

However, the reaction does not lead exclusively to cyanuric acid, but yields various by-products, notably the aminotriazines ammelide, ammeline and melamine. By employing the latest improvements in processing and reactor design, the urea pyrolysis can be optimized whereby a product is obtained assaying at about 80% cyanuric acid; about 17% ammelide; about 2% ammeline and less than about 1.0% melamine. This crude material is treated with an acidic aqueous solution such as digestion with dilute aqueous mineral acid whereby the aminotriazines are hydrolyzed to cyanuric acid. The resulting slurry is separated, washed free of acid and dried to give essentially pure cyanuric acid. For a fuller treatment on the chemistry and manufacture of cyanuric acid, reference is made to Kirk-Othmer Encyclopedia of Chemical Technology, Vol. 20, 2nd Revised Ed. 1969, pages 662 – 671 and to the bibliography appended thereto.

Although the manufacture of cyanuric acid by the pyrolysis of urea is a generally successful commercial process, there is still considerable need for improvement in handling the waste stream which remains after separating the cyanuric acid from the acid digestion. Such waste stream, commonly referred to as waste digester acid, is an acidic aqueous solution containing ammonium salts, triazines of the group, cyanuric acid and aminotriazines and iron. A representative plant specimen produced from mineral acid digestion consists essentially of about 10 to 20% by weight of the mineral acid; about 4 to 8% by weight of an ammonium salt of said acid; about 1 – 4% by weight of the triazines ammelide, cyanuric acid, ammeline and melamine in increasing order of concentration plus about 50 – 75 ppm of iron while the remainder is water. Considering that the nitrogen assay of waste digester acid discharged from a modern cyanuric acid plant is about one pound of total nitrogen (Kjeldahl) per 10 – 20 pounds of product, the loss in valuable nitrogen compounds, that is, ammonium salts and triazines, is indeed substantial.

There have been proposals for recovering nitrogen values from triazine waste streams. For instance, in USSR Pat. No. 345,103, there is described a process of treating alkaline waste streams containing melamine, ammeline, ammelide and cyanuric acid by contacting the streams with carbon dioxide to reduce the pH to about 8 whereby most of the triazines are precipitated; melamine is isolated as its cyanurate salt. After separation of precipitated triazines, alkali is added to the filtrate and the mixture heated at 120°–200° C to hydrolyze the remaining dissolved triazines to ammonia, carbon dioxide and water. Final traces of triazines are removed by adsorption on activated carbon after which the waste waters are essentially free of organics and can be discharged into the environment.

If the process aforesaid is applied to the acidic waste digester liquor from a cyanuric acid plant, the precipitated triazines will contain iron which is substantially insoluble at a pH in excess of about 7. Such iron contaminated triazines are unsuitable for recycling to the digester because the iron accumulates in the process thereby imparting undesirable color in the recovered cyanuric acid and in the chlorinated cyanurates manufactured therefrom. Moreover, the need to subject the filtrate from the triazine recovery to a post alkaline hydrolysis followed by treatment with activated charcoal, seriously impedes the commercial prospects of the patented process, even allowing for recovery of by-product ammonia.

It is thus evident that the treatment proposed in the Russian patent, is not applicable to triazine recovery from waste streams formed by acid digestion of cyanuric acid. A similar technique for precipitating triazines from melamine alkaline waste liquors is set forth in U.S. Pat. No. 3,325,493, except the filtrates are not post treated to remove soluble triazines. Of course, both of the patented processes are economically weak in that the large amounts of alkali required to maintain the high pH reaction medium, add substantially to plant overhead.

It is also known to obtain triazine values from other waste sources such as the acidic effluent of a chlorinated isocyanurate plant. In this procedure, residual chlorinated isocyanurates dissolved in the effluent are converted into the less soluble non-chlorinated derivatives such as cyanuric acid or the even more insoluble mono-sodium cyanurate which are then separated and recycled back to the chlorinator. Examples of these procedures are described in U.S. Pat. No. 3,878,208 in which the cyanuric acid is formed by dechlorination of the chlorinated isocyanurate with hydrogen peroxide and in U.S. Pat. No. 3,835,136, in which strong acid is used to effect dechlorination. Some residual organics remain in the filtrates after removal of solids.

In all of the processes aforesaid of recovering triazines from waste streams, there is one common denominator, namely, only part of the waste stream is utilized. That is to say, after the solids are separated, there still remains a filtrate or secondary effluent containing dissolved substances. As environmental restrictions move toward lower nitrogen loading for chemical effluents, the disposal of waste digester acid, even after substantially removing dissolved triazines, poses a serious challenge. Not only do the prior processes fail to meet this challenge, they complicate the situation by introducing additional contaminants such as inorganic salts formed by neutralizing the waste stream to change its pH and large amounts of spent carbon adsorbent which in itself must be processed or in some way treated.

Manifestly, the full and complete utilization of the waste digester acid of a cyanuric acid plant has yet to be realized.

In accordance with the present invention, it has been discovered that in the manufacture of cyanuric acid wherein urea is pyrolyzed to produce crude cyanuric acid and the crude cyanuric acid treated with an aqueous acidic solution to give purified cyanuric acid and waste digester acid containing dissolved ammonium salts, triazines of the group, cyanuric acid and aminotriazines and iron, such waste digester acid can be converted into useful products thereby eliminating the need of disposing of said stream comprising the steps: (a) adjusting the pH of the waste stream to a range of about 2.5 to about 4.0 by contacting it with ammonia whereby there is precipitated a major amount of the triazines and a minor amount of the iron; (b) separating the precipitated triazines and iron from the aqueous solution containing ammonium salts of the mineral acid and the remainder of iron and triazines; and (c) recovering the aqueous solution of iron and triazines from step (b).

In carrying out the process of the invention, the waste digester acid from the acid digestion of crude cyanuric acid is mixed with ammonia while agitating the reactants. Either gaseous or aqueous ammonia is satisfactory. By keeping the pH in the range of about 2.5 to 4.0, it is possible to effect precipitation of a major amount of the triazines and a minor amount of iron. As understood herein, a major amount when applied to a waste digester acid component means at least 50% by weight while a minor amount means less than 50% by weight.

The co-precipitation of iron can be prevented or at least greatly suppressed by ammoniating the waste liquor in the presence of a chelating agent, such as citric acid, capable of forming a soluble iron complex. However, this adds to the cost of the process and the presence of the chelating agent may reduce the nitrogen assay of some of the recovered products. The precipitated triazines are isolated from the ammoniated reaction mixture by the usual procedures for separating solids from a liquid substrate such as filtration, centrifugation, decantation, or the like.

The process of the invention is applicable to batch and continuous operations. Generally, its greatest utility is realized when incorporated as an adjunct in the continuous large scale manufacture of cyanuric acid in which precipitated triazines from the ammonification are recycled back to the acid digester for conversion into cyanuric acid.

As previously pointed out, the waste digester acid discharged from the digestion of cyanuric acid is an acidic aqueous solution containing dissolved triazines of the group cyanuric acid and aminotriazines, iron and ammonium salts formed by the acid hydrolysis of the aminotriazines in the crude cyanuric acid. Generally, the acid used in current commercial practice is sulfuric acid although other mineral acids, notably, phosphoric acid are entirely satisfactory.

The filtrate remaining after separating the precipitated solids from the ammoniated waste streams in accordance with the process herein is an aqueous solution of unprecipitated iron and triazines, primarily cyanuric acid with only trace amounts of ammelide and ammeline and perhaps a trace of melamine plus ammonium salts. The composition of the ammonium salts, that is, whether acid or neutral salts will vary with the pH of the ammoniated waste stream. Thus, where sulfuric was used in the digestion, the ammonium salts in ammoniated waste stream will be a mixture of ammonium sulfate and ammonium bisulfate.

Generally, the ammoniated filtrate consists by weight of from about 15% to about 40% of ammonium salts; about 0.15% to about 0.2% of residual triazines and from about 6 ppm to about 50 ppm of iron. Such solution of ammonium salts is a valuable source of available nitrogen in formulating chemical fertilizers.

The process of the present invention thus provides an answer as to what to do with the enormous volume of non-disposable waste digester acid from the manufacture of cyanuric acid by converting it into useful and valuable products. This overcomes the environmental difficulty while realizing economic gains.

The following non-limiting examples illustrate the invention in greater detail. All parts are by weight unless otherwise stated.

EXAMPLES 1–8

A specimen of waste digester acid, taken from the digester filtrate of a commercial cyanuric plant, was analyzed and found to have the following specifications:

| | |
|---|---|
| $H_2SO_4$ | 21.38% |
| $NH_4HSO_4$ | 5.0% |
| $(NH_4)_2SO_4$ | 0.0% |
| Cyanuric Acid | 0.27% |
| Ammelide | 0.49% |
| Ammeline | 0.13% |
| Melamine | 0.0% |
| Water | & Remainder % |
| pH | 0.5 |

Each of several samples of the digester acid aforesaid was treated with ammonium hydroxide (28% free ammonia) and the pH adjusted to increasing levels up to 4.5. After reaching the desired pH for a given sample, the reaction mixture was allowed to equilibrate for at least 24 hours at 23° C, with any solid phase that was formed. At the end of this period, each of the ammoniated reaction mixtures was filtered to remove solids and the filtrate analyzed by UV spectrophotometer. The analytical results are summarized in Table 1.

As is clearly demonstrated by the data of Table 1, the ammoniation of waste digester acid to a pH range of 2.5 to 4.0 reduces the dissolved triazines from an initial level of 0.89% to 0.2% corresponding to a triazine recovery of about 80%. The triazine solids can then be recycled back to the acid digester for conversion of the aminotriazines into cyanuric acid.

TABLE I

COMPOSITION (%) OF WASTE DIGESTER ACID AFTER AMMONIATION AND SOLIDS REMOVAL

| Example | pH | Ammelide | Cyanuric Acid | Ammeline | Melamine | Total Triazines |
|---|---|---|---|---|---|---|
| Untreated Digester Acid | 0.5 | 0.49 | 0.27 | 0.13 | 0 | 0.890 |
| 1 | 1.0 | 0.37 | 0.27 | 0.11 | 0 | 0.700 |
| 2 | 1.5 | 0.18 | 0.22 | 0.08 | 0 | 0.480 |
| 3 | 2.0 | 0.05 | 0.20 | 0.04 | 0 | 0.290 |
| 4 | 2.5 | 0.019 | 0.16 | 0.023 | 0 | 0.290 |
| 5 | 3.0 | 0.012 | 0.18 | 0.013 | 0 | 0.202 |
| 6 | 3.5 | 0.010 | 0.16 | 0.005 | 0 | 0.205 |
| 7 | 4.0 | 0.002 | 0.18 | 0.006 | 0 | 0.188 |
| 8 | 4.5 | 0.014 | 0.17 | 0.002 | 0 | 0.186 |

After removal of all solids from the ammoniated waste digester acid, the remaining filtrate consists of a water solution of ammonium sulfate containing traces of dissolved triazines and iron. It can be applied directly to crops as a nitrogen fertilizer or used for any purpose requiring a source of ammonium sulfate.

EXAMPLE 9

A filtrate specimen obtained from the ammoniated waste digester acid of the examples aforesaid was treated with aqueous ammonia to a pH of 5.5 and then placed in a rotary vacuum flask and evaporated to dryness; 50° C at 20 mm. The resulting ammonium sulfate assayed as follows:

| | |
|---|---|
| Ammeline | 0.02% |
| Ammelide | 0.05% |
| Cyanuric Acid | 0.02% |
| Nitrogen | 21.1% |
| Nitrogen; theory based on $(NH_4)_2SO_4$ | 21.2% |

The analytical results clearly show that high purity by-product ammonium sulfate can be recovered from waste digester acid by the process of the invention. Moreover, the crystal size of the recovered material is essentially identical to reagent grade ammonium sulfate synthesized from reagent grade ammonia and sulfuric acid.

EXAMPLES 10 – 23

The procedure for Examples 1 – 8 was repeated but in this case the purpose was to determine the iron concentration of the filtrate after ammoniating the waste liquor at various pH levels and removal of the precipitated triazines. The iron assay was carried out using atomic adsorption. The analytical results are summarized in Table II below.

TABLE II

NEUTRALIZATION OF WASTE DIGESTER ACID WITH AMMONIA (23° C)

| Example | pH | % Iron Remaining in Solution |
|---|---|---|
| Untreated Digester Acid | 0.5 | 100 |
| 10 | 2.0 | 96.3 |
| 11 | 2.5 | 94.1 |
| 12 | 3.0 | 91.3 |
| 13 | 3.5 | 88.1 |
| 14 | 4.0 | 82.4 |
| 15 | 4.5 | 33.0 |
| 16 | 5.0 | 20.1 |
| 17 | 5.5 | 16.8 |
| 18 | 6.0 | 1.15 |
| 19 | 6.5 | 0.50 |
| 20 | 7.0 | 0.46 |
| 21 | 7.5 | 0.46 |
| 22 | 8.0 | 0.16 |
| 23 | 8.5 | 0.16 |

As is evident from the analytical data of Table II, almost all of the iron remains in solution provided the digester waste liquor is ammoniated while confining the pH to the range of about 2.5 – 4.0. However, once the upper pH range is appreciably exceeded, iron precipitation builds up rapidly. For instance, ammoniation at pH 4.0 (Example 14) resulted in 82.4% of the iron remaining in solution. At pH 4.5 (Example 15) a mere 33.0% of the iron remains dissolved, a reduction of about 2½ times.

By operating in accordance with the process of the present invention, most of the triazines can be recovered from the waste liquor with minimal iron contamination.

What is claimed is:

1. In the manufacture of cyanuric acid wherein urea is pyrolyzed to produce crude cyanuric acid and the crude cyanuric acid treated with an acidic aqueous solution to give purified cyanuric acid and waste digester acid consisting essentially of a water solution of said mineral acid containing dissolved triazines of the group cyanuric acid and aminotriazines and ammonium salts and iron, the improvement of converting the waste stream into useful products thereby eliminating the need of disposing of said stream comprising the steps:

a. adjusting the pH of the waste digester acid to a range of about 2.5 to about 4.0 by contacting it with ammonia whereby there is precipitated a major amount of the triazines and a minor amount of the iron;

b. separating the precipitated triazines and iron from the aqueous solution containing ammonium salts of the mineral acid and the remainder of iron and trizines; and c. recovering the aqueous solution of ammonium salts, iron and triazines from step (b).

2. The method of claim 1 wherein the mineral acid is selected from the class consisting of sulfuric and phosphoric acids.

3. The method of claim 2 wherein the mineral acid is sulfuric.

4. The method of claim 2 wherein the mineral acid is phosphoric acid.

5. The method of claim 1 wherein the aqueous solution is evaporated to produce a solid consisting substantially of crystalline ammonium salts of the mineral acid and the remainder of the triazines and iron.

6. The method of claim 5 wherein the evaporation is carried out at sufficiently high pH whereby ammonium salts are produced having at least two hydrogen atoms replaced with ammonium.

* * * * *

UNITED STATES PATENT OFFICE
CERTIFICATE OF CORRECTION

PATENT NO. : 3,996,224
DATED : December 7, 1975
INVENTOR(S) : Charles A. Gray, et al It is certified that error appears in the above-identified patent and that said Letters Patent are hereby corrected as shown below:

```
Column 5, Table I, column under TOTAL TRIAZINES,
"0.890    should read -- 0.890
 0.700                   0.700
 0.480                   0.480
 0.290                   0.290
 0.290                   0.202
 0.202                   0.205
 0.205                   0.175
 0.188                   0.188
 0.186"                  0.186--
```
Column 6, line 50, claim 1 (b), "trizines" should read --triazines--.

Signed and Sealed this

Third Day of May 1977

[SEAL]

Attest:

RUTH C. MASON
Attesting Officer

C. MARSHALL DANN
Commissioner of Patents and Trademarks